United States Patent [19]

Bréard

[11] Patent Number: 5,011,484
[45] Date of Patent: Apr. 30, 1991

[54] SURGICAL IMPLANT FOR RESTRICTING THE RELATIVE MOVEMENT OF VERTEBRAE

[76] Inventor: Francis H. Bréard, 13, rue Friant, 75014 Paris, France

[21] Appl. No.: 418,661

[22] Filed: Oct. 10, 1989

[51] Int. Cl.$^5$ .......................... A61B 17/56; A61F 2/44
[52] U.S. Cl. ........................................ 606/61; 623/17
[58] Field of Search ............... 623/17; 606/61; 128/69

[56] References Cited

U.S. PATENT DOCUMENTS 2,677,369  5/1954  Knowles ................................ 606/61
3,648,691  3/1972  Lumb et al. ........................... 606/61

FOREIGN PATENT DOCUMENTS 3113142  1/1982  Fed. Rep. of Germany ........ 128/69

*Primary Examiner*—Ronald Frinks
*Attorney, Agent, or Firm*—Anthony J. Casella; Gerald E. Hespos

[57] ABSTRACT

The present invention relates to a surgical implant designed to prevent mutual contact between vertebrae during flexions of the vertebral column, an implant which consists of an insert (1) shaped and dimensioned so that it can be inserted, in its longitudinal direction, between the vertebral spines (A) of at least two successive vertebrae (V), the said insert comprising or being associated with retaining means (L) designed to hold it in place on the vertebrae, at the same time permitting the mutual separation of the latter.

Advantageously, the insert (1) has longitudinal grooves (2, 3) dimensioned to receive, with a certain amount of play, a corresponding vertebral spine (A), and the retaining means are constituted by a ligament (L) passing through transverse pierced holes, preferably two inclined, cross pierces holes (8), in the insert, and interlacing around the vertebral spines (A).

Utilization to remove painful complaints of the spinal nerves, in particular sciatica.

14 Claims, 1 Drawing Sheet

U.S. Patent    Apr. 30, 1991    5,011,484
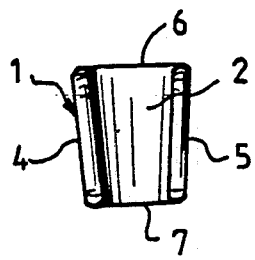
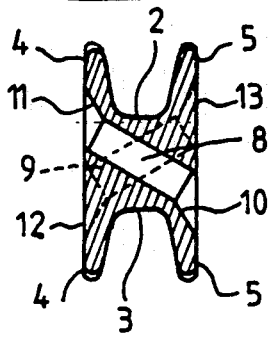
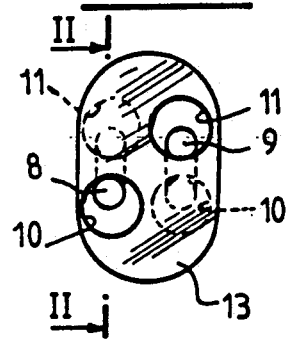
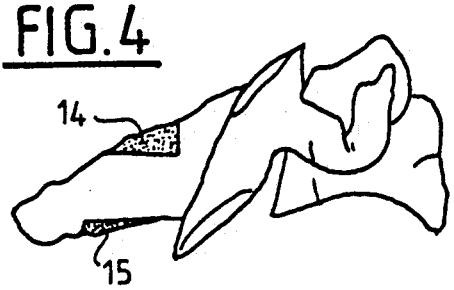
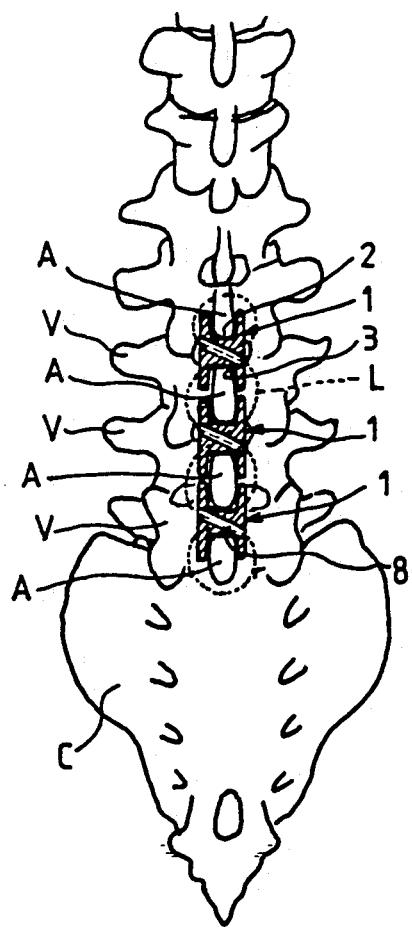
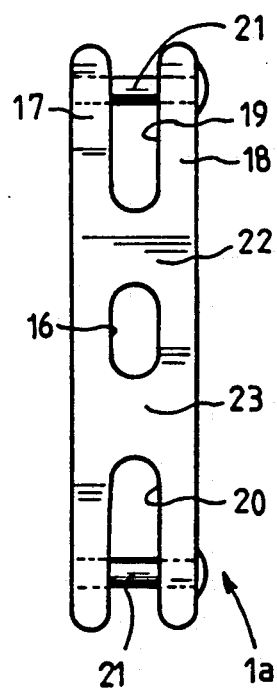
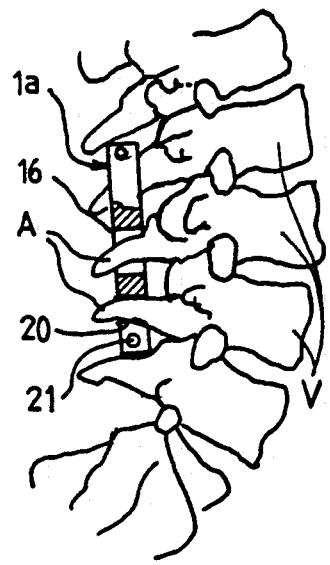

SURGICAL IMPLANT FOR RESTRICTING THE RELATIVE MOVEMENT OF VERTEBRAE

The present invention relates to a surgical implant designed to prevent contact between vertebrae during flexions of the vertebral or spinal column.

It is known that, in certain subjects whose intervertebral disks have undergone considerable wear, the spinal nerves passing between the vertebrae are inevitably crushed through the effect of the mutual hard contact between the latter, occurring during extreme flexions of the vertebral column forwards or backwards. This crushing of the spinal nerves gives rise to extremely painful complaints, the most common of which is sciatica.

To eradicate this type of complaint, it is known to attach spines of the vetebra together using small metal plates which permanently maintain a sufficient gap between the vertebrae. However, of course, by prohibiting any relative movement of the vertebrae, this operation causes considerable discomfort to the patient, even if, quite often, it affects only a limited portion of the vertebral column which is generally the one covering the lumbar region.

There is also known a technique consisting in interlacing an artificial ligament around the spines of the vertebrae. However, this technique, while enabling the vertebrae to retain a certain relative degree of mobility, has simply the effect of preventing contact between the vertebrae at the front and is thus far from solving the problem of crushed spinal nerves, which is chiefly posed at the back.

That is why the present invention proposes to solve this problem with the help of a surgical implant which is characterized in that it includes an inter-vertebral insert that can be introduced between the spines of at least two successive vertebrae, as well as retaining means, integral with or independent of the insert, to hold it in place in relation to said spines, there being a possibility of heightwise relative deflection for the latter.

As it will be readily appreciated, this insert, once in place, limits the degree whereby the spines of the vertebrae move towards one another during rearwards flexion of the vertebral column, in order to prevent in this way any contact between the vertebrae in their rear portions, that is to say where the problem of spinal nerve crushing is most acute.

Conversely, during forward flexion of the vertebral column, the vertebrae can freely move away from one another so that the patient will experience hardly any discomfort following the implanting in his or her back of an insert according to the invention.

In practice, the means for retaining the insert will be designed to restrict the separating movement of the spines of the vertebrae in order to prevent contact between vertebrae at the front, which is also liable to cause crushing of certain spinal nerves, but, even with such a movement restriction, the discomfort experienced is perfectly tolerable for the patient.

In its simplest form the vertebral insert according to the invention is formed by a stud that is insertable between the spines of two successive vertebrae. If necessary, it will, of course, be possible to implant several individual inserts of this type over the entire length of a section of the vertebral column including more than two vertebrae, such as the lumbar section.

According to one variant of the invention, the insert is pierced right through in its direction of insertion by a hole into which a corresponding vertebral spine can be introduced.

The insert is thus operative between at least three vertebrae at a time without making it impossible for the vertebral spines of the latter to move apart from one another.

Advantageously, the insert has, on one and/or the other of the opposite two end faces, a groove for receiving and guiding a corresponding spine, over-dimensioned in relation to the latter, the said groove preferably having a width progressively decreasing from one end to the other to conform to the naturally tapering shape of the spine that it receives.

According to another advantageous characteristic of the invention, the insert comprises one or more pierced holes transverse to its direction of insertion, and preferably, two inclined, crossed holes open at their two ends.

This type of vertebral insert is used when the retaining means are constituted by a continuous artificial ligament. This ligament, which is loosely interlaced around the spines of the vertebrae by passing it through the pierced holes of the insert or inserts, ensures, thanks to its own elasticity, that the vertebrae come flexibly to a halt during forward flexion of the vertebral column.

To ensure that this ligament is not nicked during these movements performed by the vertebrae, it is preferably provided, according to the invention, for each of the transverse pierced holes to terminate at each end in a flared opening.

According to another embodiment of the invention, the insert is extended on either side of the groove or of at least one of the grooves, by two high lateral arms joined in the vicinity of their free ends by a pin. The said pin constitutes an alternative form of embodiment of the retaining means by delimiting, with said lateral arms and the bottom of the groove a space for receiving a corresponding vertebral spine there being scope for heightwise deflection.

The advantage of this alternative embodiment of the retaining means is that it is directly integrated in the insert, which obviates the need for any additional operation, as is the case when an artificial ligament is used.

Several embodiments of the present invention will now be described in greater detail, but solely by way of non limitative examples, with reference to the annexed drawings, wherein:

FIG. 1 is a plan view of an inter-vertebral insert according to a first embodiment of the invention;

FIG. 2 is a cross-sectional view along line II—II of FIG. 3;

FIG. 3 is a side view of the same inter-vertebral insert;

FIG. 4 is a representation of a vertebra reshaped for the implantation of an inter-vertebral insert;

FIG. 5 shows, in rear view, the lower portion of a vertebral column on which several inter-vertebral inserts in accordance with the first embodiment of the invention have been implanted.

FIG. 6 is a front view of an inter-vertebral insert according to a second embodiment; and FIG. 7 illustrates the implantation, in the lower portion of the vertebral column, of an insert according to FIG. 6, represented in partial cross-section.

The inter-vertebral insert 1, represented in FIGS. 1 to 3, takes the form of a small stud provided on its upper and lower faces, with a corresponding longitudinal groove, 2 or 3, delimited by low lips 4 and 5 which as viewed from the side, have the shape of an arc of a circle (FIG. 3). As shown in FIG. 1, the width of each groove 2 or 3 decreases progressively between a front face 6 and a rear face 7 of insert 1.

In addition, and as shown in FIGS. 2 and S, the central portion of inter-vertebral insert i comprises two transverse pierced holes 8, 9, inclined and crossed each emerging at their two ends, in outwardly flared openings 10, 11, on the lateral faces 12, 13 of insert 1. As clearly shown in FIG. 3, the holes 8, 9 are simply provided side by side without there being any communication between them.

An insert 1, as described above, is dimensioned to be inserted between the spines of two successive vertebrae. Each vertebral spine is then housed, with a slight amount of lateral play, in a corresponding groove 2 or 3 of the insert, after being recalibrated as shown in FIG. 4, on which the fragments of bone cut away are seen as dark areas bearing the reference numbers 14 and 15.

As shown in FIG. 5, several inserts, such as 1, can be implanted individually between the successive spines A of the vertebrae V of a given section of the vertebral column, the lumbar section in the Present case. In this case, the inserts 1, positioned one above the other, are held in place by a continuous artificial ligament L, which is passed through the holes 8, 9 of each of the said inserts, where it is crossed over itself each time, and which is passed loosely around the spines of the two end lumbar vertebrae. Below the lower lumbar vertebra, ligament L can, alternatively, be clipped to the coccyx C.

Once this operation has been performed, the different inserts 1 restrict the movement whereby the vertebral spines move toward one another during rearward flexion of the vertebral column, thus preventing any hard contact between the vertebrae, hence removing any risks of crushing to the spinal nerves passing between the said vertebrae, lips 4, 5 of the inserts then playing the part, during this approach movement, of lateral guide members. In the event of flexion of the vertebral column in the opposite direction, the spines of the vertebrae can move away from one another, while remaining inside grooves 2, 3 of the inserts, until the two end vertebral spines come into flexible contact with ligament L, which thus restricts the approach movement of the front heads of the vertebrae, here again to prevent any crushing of the spinal nerves located at this point.

FIG. 6 represents an inter-vertebral insert 1a according to a second embodiment of the invention, the central body of which is pierced by a vertically oblong, longitudinal hole 16. This longitudinal hole 16 is dimensioned to receive a vertebral spine, reshaped as represented in FIG. 4, with a certain heightwise deflection clearance. This inter-vertebral insert also has, at its upper and lower ends, corresponding grooves 19, 20 that are far deeper than grooves 2, 3 of insert 1 in the first embodiment. The high arms, 17, 18, delimiting each of these grooves 19, 20 are joined, in the vicinity of their free ends,by a removable metallic pin 21. This pin delimits, with the bottom of the groove and the associated arms 17, 18, a space for receiving a vertebral spine, also dimensioned to permit the latter a certain degree of heightwise deflection.

FIG. 7 shows that, in order to implant the insert that has just been described in the vertebral column, it suffices to introduce three spines A of adjacent vertebrae V respectively in the oblong longitudinal hole 16 and in the two grooves 19, 20 closed by the pins 21. The two portions, 22, 23, of the insert will then play the part of two individual successive inserts 1 in FIG. 6, while pins 21 will perform substantially the same function as artificial ligament L.

In order to implant inserts i or ia in the vertebral column, it will, of course, be necessary, as a preliminary, to cut the natural ligaments joining the vertebrae affected by this implantation.

For the sake of completeness, it should be specified that each of the inserts described above will, preferably, be made of a plastic material having a low friction coefficient, such as polytetrafluoroethylene, to facilitate the sliding of the spines of the vertebrae inside the inserts.

It also goes without saying that, on the basis of the principle of the present invention, various other embodiments thereof could also be contemplated.

Thus, in an insert 1 as represented in FIGS. 1 to 3, the lips 4, 5 could be extended upwardly and downwardly to be joined like the lateral arms of the insert in FIG. 6, by a stop pin. Furthermore, the insert 1a of FIG. 6, with its oblong, longitudinal hole 16, could be provided with spine receiving grooves identical with the grooves 2, 3 of insert 1 in FIGS. 1 to 3, in which case, it would, of course, be necessary to provide, in order to restrict the separation of the outer spines as in FIG. 5, for a ligament passing through transverse pierced holes, inclined and crossed, located in portions 22, 23 of insert 1a.

What is claimed is:

1. Surgical implant designed to prevent mutual contact between vertebrae during flexions of the vertebral column characterized in that the implant includes an intervertebral insert (1a) insertable between the vertebral spines (A) of at least two successive vertebrae (V), the insert (1a) being pierced right through in its direction of insertion by a hole (16) to permit the passage of a corresponding vertebral spine (A), retaining means (21) to hold the insert in place in relation to the said vertebral spines, there being a possibility of heightwise relative deflection for the latter.

2. Surgical implant according to claim 1 characterized in that the insert has, on two opposite end faces, a groove (19, 20) for receiving and guiding a corresponding vertebral spine (A), overdimensioned in relation to the said spine.

3. Surgical implant according to claim 2, characterized in that the insert (1a) is extended, on either side of the groove (19, 20), by two high lateral arms (17, 18) which are joined, in the vicinity of their free ends, by a pin (21) constituting the said retaining means by delimiting, with the said lateral arms and the bottom of the groove, a space for receiving with a degree of play a corresponding vertebral spine (A).

4. Surgical implant for preventing mutual contact between vertebrae during flexions of the vertebral column, characterized in that the implant includes an intervertebral insert insertable between the vertebral spines of at least two successive vertebrae, the insert further comprises at least one drilled hole transverse to its direction of insertion and open at two ends and retaining means defining at least one ligament for holding the insert in place in relation to the vertebral spines, the holes in the insert to permit the passage of the said ligament, there being a possibility of heightwise relative deflection of the vertebral spines.

5. Surgical implant according to claim 4, characterized in that the insert comprises two inclined, crossed pierced holes (8, 9).

6. Surgical implant according to claim 5, characterized in that each of the pierced holes (8, 9) is terminated, at each end, by a flared opening (10, 11).

7. Surgical implant for preventing mutual contact between vertebrae of a vertebral column during flexions of the vertebral column, said surgical implant comprising:

an inter-vertebral insert means insertable between vertebral spines of successive vertebrae which form a section to be treated of the vertebral column, said inter-vertebral insert means having two end surfaces for respectively contacting the spines of the end vertebrae of said section of the vertebral column; and retaining means associated with said inter-vertebral insert means and having portions to be passed over said spines of said two end vertebrae, said portions of said retaining means being so distant from the end surfaces of said inter-vertebral insert means that the retaining means allow the vertebrae to have a relative limited movement away from each other upon forward flexion of the vertebral column.

8. Surgical implant according to claim 7, characterized in that said inter-vertebral insert means comprises a plurality of individual insert members, each of which is insertable between two respective vertebrae of said section and has, on one of the two opposite end surfaces, a groove which is over-dimensioned in relation to a corresponding vertebral spine, in order to freely receive and guide the vertebral spine.

9. Surgical implant according to claim 8, characterized in that each groove (2, 3) has a width that decreases progressively from one end to the other.

10. Surgical implant according to claim 8, characterized in that the retaining means include a ligament and each said insert member comprises at least one hole formed transverse to the direction of insertion of the insert and open at their two ends to permit the passage of the said ligament.

11. Surgical implant according to claim 10, characterized in that the insert member comprises two inclined, crossed holes.

12. Surgical implant according to claim 11, characterized in that each of the holes is terminated, at each end, by a flared opening.

13. Surgical implant according to claim 8, characterized in that the insert member comprises, on either side of each said groove, two high lateral arms which are joined, in the vicinity of their free ends, by a pin constituting the said retaining means by delimiting, with said lateral arms and the bottom of the groove, a space for receiving with a lateral play a corresponding vertebral spine.

14. Surgical implant according to claim 13, characterized in that the insert member is provided right through in its direction of insertion with a hole to permit the passage of the vertebral spine of a corresponding intermediate vertebra of said section to be treated of the vertebral column.

* * * * *